United States Patent
McLeod

(10) Patent No.: US 12,213,830 B2
(45) Date of Patent: Feb. 4, 2025

(54) METHOD AND SYSTEM FOR AUTOMATICALLY DETECTING AN ULTRASOUND IMAGE VIEW AND FOCUS TO PROVIDE MEASUREMENT SUITABILITY FEEDBACK

(71) Applicant: GE Precision Healthcare LLC, Wauwatosa, WI (US)

(72) Inventor: Kristin Sarah McLeod, Oslo (NO)

(73) Assignee: GE Precision Healthcare LLC, Waukesha, WI (US)

(*) Notice: Subject to any disclaimer, the term of this patent is extended or adjusted under 35 U.S.C. 154(b) by 0 days.

(21) Appl. No.: 17/192,005

(22) Filed: Mar. 4, 2021

(65) Prior Publication Data

US 2022/0280133 A1    Sep. 8, 2022

(51) Int. Cl.
*A61B 8/00* (2006.01)
*A61B 8/08* (2006.01)

(52) U.S. Cl.
CPC ............. *A61B 8/08* (2013.01); *A61B 8/461* (2013.01); *A61B 8/5207* (2013.01)

(58) Field of Classification Search
CPC ......... A61B 8/08; A61B 8/461; A61B 8/5207; A61B 8/5223; A61B 8/0883; A61B 8/463; A61B 8/5215; A61B 8/523; G06N 3/08; G06T 7/0012; G06T 7/13; G06T 7/62; G06T 2207/10132; G06T 2207/20081; G06T 2207/20084; G06T 2207/30048

See application file for complete search history.

(56) References Cited

U.S. PATENT DOCUMENTS

| | | | |
|---|---|---|---|
| 2009/0034808 A1* | 2/2009 | Zhou ................. | G06F 18/214 382/128 |
| 2009/0074280 A1* | 3/2009 | Lu .................... | A61B 8/00 382/131 |
| 2018/0028161 A1 | 2/2018 | Guenette et al. | |
| 2018/0310920 A1 | 11/2018 | Specht et al. | |
| 2019/0000424 A1 | 1/2019 | Samset | |
| 2019/0125298 A1* | 5/2019 | Abolmaesumi ......... | G06N 3/08 |
| 2019/0130554 A1* | 5/2019 | Rothberg ............ | G06T 7/0002 |
| 2019/0388060 A1* | 12/2019 | Aase ................. | A61B 8/543 |
| 2021/0035286 A1* | 2/2021 | Yoo .................. | G06V 10/20 |

* cited by examiner

*Primary Examiner* — Joel Lamprecht
*Assistant Examiner* — James F McDonald, III
(74) *Attorney, Agent, or Firm* — McAndrews, Held & Malloy, Ltd.; Daniel Bissing; David Bates

(57) ABSTRACT

A system and method for automatically detecting an ultrasound image view and focus to provide feedback on measurement suitability is provided. The method includes acquiring, by an ultrasound system, an ultrasound image of a target. The method includes automatically identifying, by at least one processor of the ultrasound system, an ultrasound image view and focus based on detected anatomical structures in the ultrasound image. The method includes automatically selecting, by the at least one processor, at least one measurement associated with the ultrasound image view. The method includes assigning, by the at least one processor, a measurement grade for each of the at least one measurements based on an ability to accurately perform each of the at least one measurement in the ultrasound image. The method includes causing, by the at least one processor, a display system to present the measurement grade for each of the at least one measurement.

20 Claims, 4 Drawing Sheets

METHOD AND SYSTEM FOR AUTOMATICALLY DETECTING AN ULTRASOUND IMAGE VIEW AND FOCUS TO PROVIDE MEASUREMENT SUITABILITY FEEDBACK

FIELD

Certain embodiments relate to ultrasound imaging. More specifically, certain embodiments relate to a method and system for automatically detecting an ultrasound image view and focus to provide feedback on measurement suitability.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

During an ultrasound imaging procedure, an ultrasound operator may acquire ultrasound image views and perform measurements on the acquired ultrasound images. For example, in ultrasound cardiology, an ultrasound operator may acquire a four chamber (4CH) view of the heart to perform area measurements of the left atrium, right atrium, left ventricle, and/or right ventricle. Additionally or alternatively, the ultrasound operator may plan to perform length, mid diameter, and/or base diameter measurements of the right ventricle provided in the 4CH view, for example. However, in some cases, the acquired ultrasound image view may not be suitable for performing some or all of the desired measurements. For example, some of the imaged structures in an ultrasound view may be incomplete or out of focus such that the ultrasound system is unable to automatically perform the desired measurements and/or a user is unable to manually perform the desired measurements. In these cases, the ultrasound operator may have to repeat the ultrasound imaging procedure to acquire a suitable ultrasound image view, which may be frustrating and inefficient.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically detecting an ultrasound image view and focus to provide feedback on measurement suitability, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
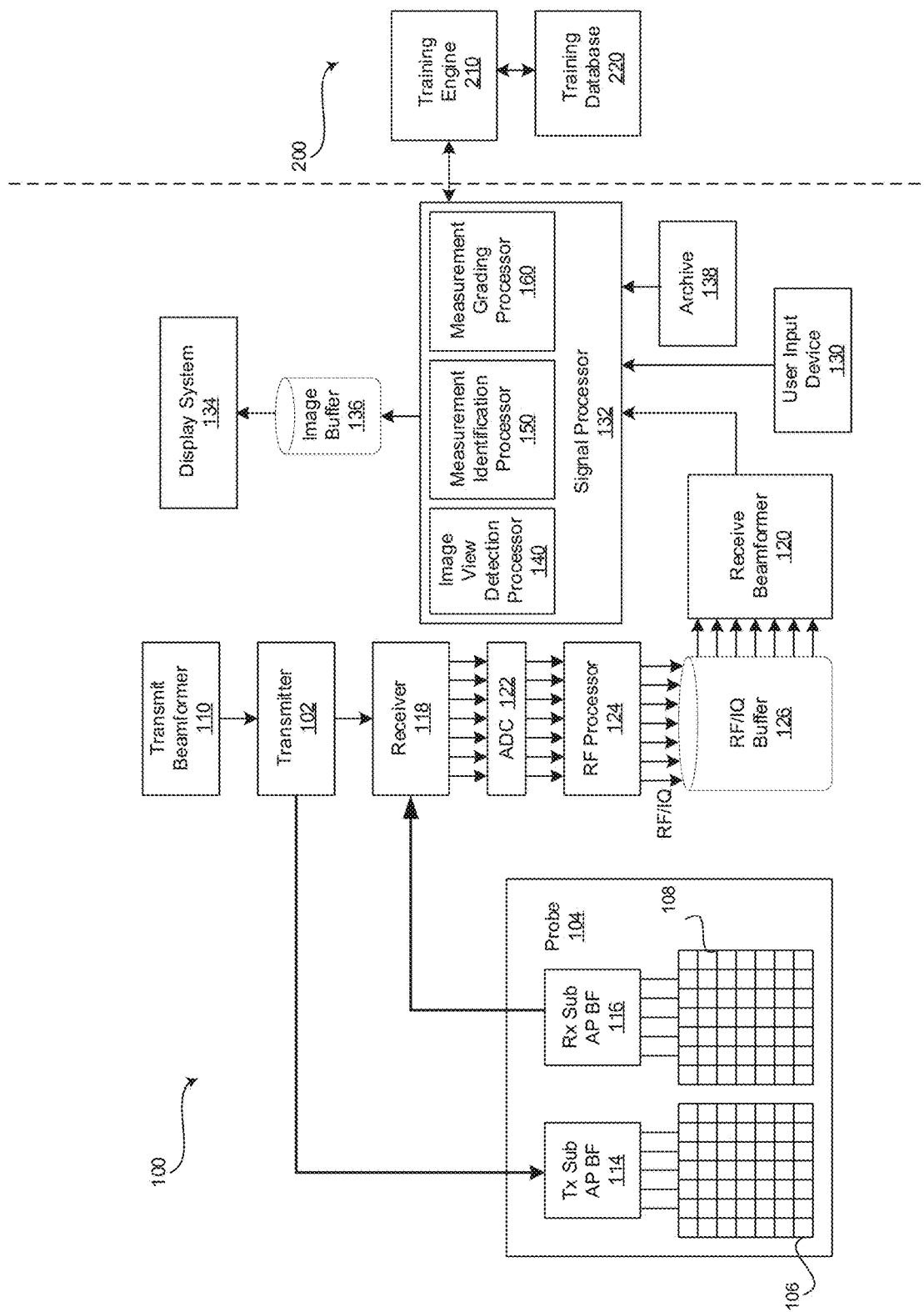
FIG. 1 is a block diagram of an exemplary ultrasound system that is operable to automatically detect an ultrasound image view and focus to provide feedback on measurement suitability, in accordance with various embodiments.

Certain embodiments may be found in a method and system for automatically detecting an ultrasound image view and focus to provide feedback on measurement suitability. Aspects of the present disclosure have the technical effect of automatically detecting an ultrasound image view and focus of an acquired ultrasound image. Various embodiments have the technical effect of presenting a list of measurements associated with anatomy present in a detected ultrasound image view. Certain embodiments have the technical effect of automatically grading a suitability of the acquired ultrasound image for performing measurements associated with the anatomy present in the detected ultrasound image view. Aspects of the present disclosure have the technical effect of presenting the ultrasound image suitability grades of the measurements associated with the anatomy present in the detected ultrasound image view in substantially real-time such that an ultrasound operator may manipulate the ultrasound probe to acquire a view with improved measurement grades and/or select to manually or automatically perform one or more of the listed measurements. Certain embodiments have the technical effect of providing immediate user feedback of ultrasound image suitability for performing measurements.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, Contrast Enhanced Ultrasound (CEUS), and/or sub-modes of B-mode and/or CF such as Harmonic Imaging, Shear Wave Elasticity Imaging (SWEI), Strain Elastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to automatically detect an ultrasound image view and focus to provide feedback on measurement suitability, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select measurements, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an image view detection processor 140, a measurement identification processor 150, and a measurement grading processor 160. The signal processor 132 may be capable of receiving input information from a user input device 130 and/or archive 138, generating an output displayable by a display system 134, and manipulating the output in response to input information from a user input device 130, among other things. The signal processor 132, image view detection processor 140, measurement identification processor 150, and measurement grading processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image view detection processor 140 that comprises suitable logic, circuitry, interfaces and/or code that may be operable to analyze acquired ultrasound images to automatically identify an ultrasound image view and focus based on detected anatomical structures in the ultrasound images. The image view detection processor 140 may include image analysis algorithms, artificial intelligence algorithms, one or more deep neural networks (e.g., a convolutional neural network) and/or may utilize any suitable form of image analysis techniques or machine learning processing functionality configured to analyze acquired ultrasound images to automatically identify an ultrasound image view and focus. For example, the image view detection processor 140 may identify a four chamber (4CH) or parasternal long-axis (PLAX) ultrasound image view based on a detected presence of anatomical structures in the particular view, such as by detecting a left ventricle, right ventricle, left atrium, right atrium, aorta, left ventricle outflow tract, and/or any suitable anatomical structures. As another example, the image view detection processor 140 may identify anatomical structures in focus based on an amount of image detail for each of the anatomical structures. The image view detection processor 140 may be configured to provide the identified ultrasound image views and focus to the measurement identification processor 150 and/or the measurement grading processor 160. The image view detection processor 140 may additionally and/or alternatively store the identified ultrasound image views and focus at archive 138 and/or any suitable data storage medium.

The image view detection processor 140 may comprise suitable logic, circuitry, interfaces and/or code that may be operable to automatically identify an ultrasound image view and focus based on detected anatomical structures in acquired ultrasound images. In various embodiments, the image view detection processor 140 may be provided as a deep neural network that may be made up of, for example, an input layer, an output layer, and one or more hidden layers in between the input and output layers. Each of the layers may be made up of a plurality of processing nodes that may be referred to as neurons. For example, the image view detection processor 140 may include an input layer having a neuron for each pixel or a group of pixels from a scan plane of a heart. The output layer may have neurons corresponding to a left ventricle, right ventricle, left atrium, right atrium, aorta, left ventricle outflow tract, and/or any suitable anatomical structures of the heart. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the image view detection processor 140 deep neural network (e.g., convolutional neural network) may identify an ultrasound image view and focus based on detected anatomical structures in acquired ultrasound images with a high degree of probability.

The signal processor 132 may include measurement identification processor 150 that comprises suitable logic, circuitry, interfaces and/or code that may be operable to automatically select one or more measurements associated with anatomical structures in the ultrasound image view identified by the image view detection processor 140. For example, ultrasound image views may each be associated with one or more potentially relevant measurements. The one or more potentially relevant measurements may be associated with one or more ultrasound image views and stored at archive 138 and/or any suitable data storage medium. For example, potentially relevant measurements associated with a 4CH view of a heart may include a left ventricle (LV) area measurement, right ventricle (RV) area measurement, left atrium (LA) area measurement, right atrium (RA) area measurement, RV length measurement, RV mid diameter measurement, RV base diameter measurement, and/or any suitable 4CH view measurement. As another example, potentially relevant measurements associated with a PLAX view of a heart may include an interventricular septum (IVS) measurement, left ventricle internal dimension (LVID) measurement, left ventricle posterior wall (LVPW) measurement, right ventricle internal dimension (RVID) measurement, left ventricle outflow tract (LVOT) measurement, left atrium (LA) measurement, aorta (Ao) measurement, and/or any suitable PLAX view measurement. The measurement identification processor 150 may be configured to select the one or more potentially relevant measurements from the archive 138 and/or any suitable data storage medium based on the association and the ultrasound image view identified by the image view detection processor 140. The measurement identification processor 150 may be configured to present the selected one or more potentially relevant measurements at the display system 134 and/or provide the selected one or more potentially relevant measurements to the measurement grading processor 160.

The signal processor 132 may include a measurement grading processor 160 that comprises suitable logic, circuitry, interfaces and/or code that may be operable to automatically analyze the ultrasound image and assign a grade for each of the selected measurements and/or associated anatomical structures based on an ability to accurately perform each measurement in the ultrasound image. The measurement grading processor 160 may include image analysis algorithms, artificial intelligence algorithms, one or more deep neural networks (e.g., a convolutional neural network) and/or may utilize any suitable form of image analysis techniques or machine learning processing functionality configured to analyze acquired ultrasound images and assign grades to selected potentially relevant measurements and/or associated anatomical structures. The measurement grading processor 160 may assign the grade based on a level of completeness of the anatomical structure to be measured, a focus level of the anatomical structure to be measured, and/or any suitable criterion related to the image quality of the anatomical structure to be measured.

The measurement grading processor 160 may comprise suitable logic, circuitry, interfaces and/or code that may be operable to assign a grade for each of the selected measurements and/or anatomical structures. In various embodiments, the measurement grading processor 160 may be provided as a deep neural network that may be made up of, for example, an input layer, an output layer, and one or more hidden layers in between the input and output layers. Each of the layers may be made up of a plurality of processing nodes that may be referred to as neurons. For example, the measurement grading processor 160 may include an input layer having a neuron for each pixel or a group of pixels from a scan plane of a heart. The output layer may have neurons corresponding to image qualities of anatomical structures of selected measurements, such as a completeness quality and a focus quality of a left ventricle, right ventricle, left atrium, right atrium, aorta, left ventricle outflow tract, and/or any suitable image qualities of anatomical structures of the heart. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the measurement grading processor 160 deep neural network (e.g., convolutional neural network) may identify image qualities of anatomical structures in acquired ultrasound images with a high degree of probability.

The measurement grading processor 160 may be configured to cause the display system 134 to present the grade derived from the image quality criterion for each of the selected measurements and/or anatomical structures. The grades may include a plurality of grade levels, such as ideal for measurement, suitable for measurement, and not suitable for measurement, or any suitable number of grade levels. The grade levels may be represented by symbols (e.g., check mark for suitable and "X" for not suitable), color-coding (e.g., green for ideal, orange for suitable, and red for not suitable), numerical grade levels, letter grade levels, text describing suitability, and/or any suitable grade level indicator. In various embodiments, the grade levels may correspond with whether the measurement may be performed automatically by the signal processor 132, whether the measurement may be performed manually by a user via the user input device 130, and/or whether the measurement may not be performed.

Figure 2:
FIG. 2 is a display of an exemplary four chamber (4CH) ultrasound image view of a heart having measurement suitability feedback, in accordance with various embodiments.

FIG. 2 is a display 300 of an exemplary four chamber (4CH) ultrasound image view 310 of a heart having measurement suitability feedback 320-336, in accordance with various embodiments. Referring to FIG. 2, the display 300 may comprise a 4CH ultrasound image view 310 and measurement suitability feedback 320-336. The measurement identification processor 150 and/or the measurement grading processor 160 may be configured to present one or more automatically selected measurements 320 associated with detected anatomical structures 330 in the identified 4CH ultrasound image view 310 at a display system 134. For example, the measurement identification processor 150 and/or the measurement grading processor 160 may present 4CH measurements 320, such as an LV area measurement, an LA area measurement, an RV area measurement, an RA area measurement, an RV mid, base, length measurement, and/or any suitable measurement. The measurement grading processor 160 may present the grade 322, 324, 326 for each of the selected measurements 320 at the display system 134. The grade levels may be represented by symbols (e.g., check mark for suitable and "X" for not suitable), color-coding (e.g., green for ideal, orange for suitable, and red for not suitable), numerical grade levels, letter grade levels, text describing suitability, and/or any suitable grade level indicator. Referring to FIG. 2, the grade symbols may include a green check mark 322 for a highest grade (.e.g., ideal), an orange check mark 324 for a middle grade (e.g., suitable), and a red "X" 326 for the lowest grade (e.g., not suitable).

Still referring to FIG. 2, the measurement grading processor 160 may provide a selectable option 328 to perform a corresponding measurement 320. For example, the selectable option 328 may indicate whether the measurement 320 may be performed automatically or manually. In various embodiments, an ability to automatically perform the measurement 320 by the signal processor 132 may be based on the measurement suitability grade 322, 324, 326. As an example, ideal measurement grades may correspond with an option to automatically perform the measurement. Suitable measurement grades may correspond with options to automatically and/or manually perform the measurement 320. Unsuitable measurement grades may correspond with options to manually perform the measurement and/or may not include a measurement option 328. In various embodiments, selection of the automatic measurement option 328 initiates an automatic measurement performed by the signal processor 132. In an exemplary embodiment, selection of the manual measurement option 328 initiates a manual measurement mode where measurement tools are presented such that an operator may manually perform the selected measurement 320. The selectable measurement option 328 may be buttons, a drop down menu, and/or any suitable selectable option. The measurement suitability feedback related to the particular measurements 320-328 may provide information to an ultrasound operator related to improvements in imaging the anatomical structures such that an ultrasound operator may manipulate the ultrasound probe 104 to acquire images 310 suitable for performing the desired measurements 320.

As shown in FIG. 2, the measurement suitability feedback 320-336 may further comprise feedback related to the anatomical structures 330 presented in the detected ultrasound image view 310. For example, the image view detection processor 140 and/or the measurement grading processor 160 may further present the detected ultrasound image view 310 and a grade 332-336 of the anatomical structures 330 provided in the ultrasound image view 310. Referring to FIG. 2, the image view detection processor 140 and/or the measurement grading processor 160 presents the identity of the detected ultrasound image view 310 and anatomical structures 330 therein. For example, the image view detection processor 140 and/or the measurement grading processor 160 may present the 4CH view identification and anatomical structures 330 present in the 4CH view, such as the LV, the LA, the RV, the RA, and/or any suitable anatomical structures present in the 4CH view. The measurement grading processor 160 may present the grade 332, 334, 336 for each of the anatomical structures 330 associated with the selected measurements 320 at the display system 134. The grade levels may be represented by symbols (e.g., check mark for suitable and "X" for not suitable), color-coding (e.g., green for ideal, orange for suitable, and red for not suitable), numerical grade levels, letter grade levels, text describing suitability (e.g., with respect to completeness and/or focus), and/or any suitable grade level indicator. Referring to FIG. 2, the grade symbols may include a green check mark 332 for a highest grade (.e.g., ideal), an orange check mark 334 for a middle grade (e.g., suitable), and a red "X" 336 for the lowest grade (e.g., not suitable). The measurement suitability feedback related to the anatomical structures 330-336 may provide information to an ultrasound operator related to improvements in imaging the anatomical structures such that an ultrasound operator may manipulate the ultrasound probe 104 to acquire images 310 suitable for performing the desired measurements 320.

Figure 3:
FIG. 3 is a display of an exemplary parasternal long-axis (PLAX) ultrasound image view of a heart of having measurement suitability feedback, in accordance with various embodiments.

FIG. 3 is a display of an exemplary parasternal long-axis (PLAX) ultrasound image view 310 of a heart of having measurement suitability feedback, in accordance with various embodiments. FIG. 3 shares various characteristics with FIG. 2 as described above. Referring to FIG. 3, the display 300 may comprise a PLAX ultrasound image view 310 and measurement suitability feedback 320-336. The measurement identification processor 150 and/or the measurement grading processor 160 may be configured to present one or more automatically selected measurements 320 associated with detected anatomical structures 330 in the identified PLAX ultrasound image view 310 at a display system 134. For example, the measurement identification processor 150 and/or the measurement grading processor 160 may present PLAX measurements 320, such as an IVS measurement, an LVID measurement, an LVPW measurement, an RVID measurement, an LVOT measurement, an LA measurement, an Ao measurement, and/or any suitable PLAX measurement. The measurement grading processor 160 may present the grade 322, 324, 326 for each of the selected measurements at the display system 134. Referring to FIG. 3, the grade symbols may include a green check mark 322 for a highest grade (.e.g., ideal) and a red "X" 326 for the lowest grade (e.g., not suitable). The measurement grading processor 160 may provide a selectable option 328 to perform a corresponding measurement 320. For example, the selectable option 328 may include options for performing measurement 320 automatically or manually. The measurement suitability feedback related to the particular measurements 320-328 may provide information to an ultrasound operator related to improvements in imaging the anatomical structures such that an ultrasound operator may manipulate the ultrasound probe 104 to acquire images 310 suitable for performing the desired measurements 320.

As shown in FIG. 3, the measurement suitability feedback 320-336 may further comprise feedback related to the anatomical structures 330 presented in the detected ultrasound image view 310. For example, the image view detection processor 140 and/or the measurement grading processor 160 may present the PLAX view identification and anatomical structures 330 present in the PLAX view, such as the LV, the LA, the LVOT, the aorta, the RV, the RA, and/or any suitable anatomical structures present in the PLAX view. The measurement grading processor 160 may present the grade 332,334,336 for each of the anatomical structures 330 associated with the selected measurements 320 at the display system 134. Referring to FIG. 3, the grade symbols may include a green check mark 332 for a highest grade (.e.g., ideal), an orange check mark 334 for a middle grade (e.g., suitable), and a red "X" 336 for the lowest grade (e.g., not suitable). The measurement suitability feedback related to the anatomical structures 330-336 may provide information to an ultrasound operator related to improvements in imaging the anatomical structures such that an ultrasound operator may manipulate the ultrasound probe 104 to acquire images 310 suitable for performing the desired measurements.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present ultrasound image views 310, the associated measurements 320 and detected anatomical structures 330, the identification of the detected view, the measurement and/or anatomical structure grades 322, 324, 326, 332, 334, 336, the selectable measurement options 328, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound image data 310, ultrasound image view detection instructions, measurements 320 and anatomical structures 330 associated with ultrasound image views 310, and measurement grading instructions, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 160 may comprise suitable logic, circuitry, interfaces and/or code that may be operable to train the neurons of the deep neural network(s) (e.g., artificial intelligence model(s)) inferenced (i.e., deployed) by the image view detection processor 140 and/or the measurement grading processor 160. For example, the artificial intelligence model inferenced by the image view detection processor 140 may be trained to automatically identify anatomical features in ultrasound images 310. As an example, the training engine 210 may train the deep neural networks deployed by the image view detection processor 140 using database(s) 220 of different classified ultrasound image views. The artificial intelligence model inferenced by the measurement grading processor 160 may be trained to automatically identify image qualities (e.g., completeness, focus, and the like) of anatomical features in ultrasound images 310. As an example, the training engine 210 may train the deep neural networks deployed by the image view detection processor 140 using database(s) 220 of classified ultrasound images 310 having different image qualities of anatomical structures to be measured.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 4:
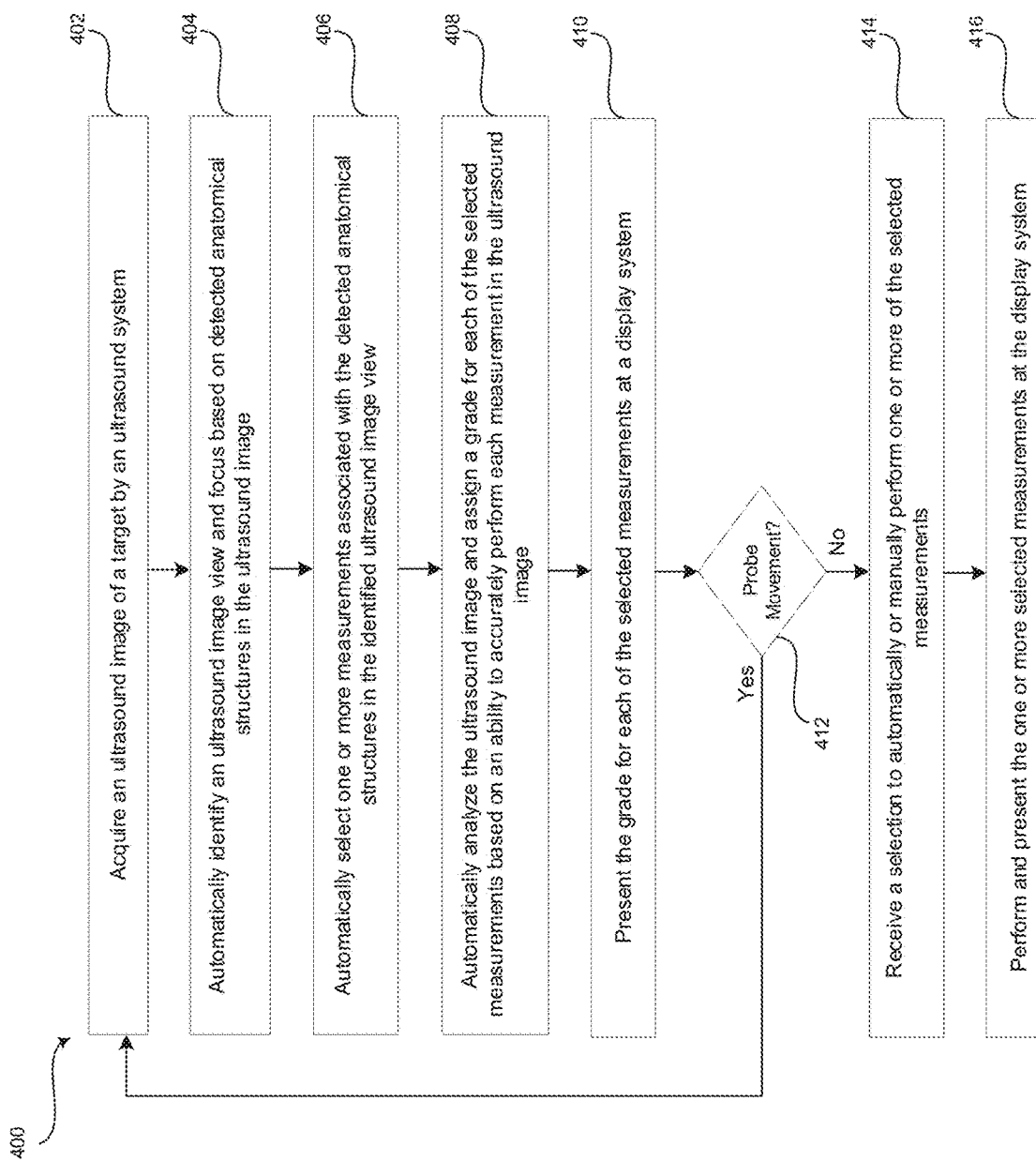
FIG. 4 is a flow chart illustrating exemplary steps that may be utilized for automatically detecting an ultrasound image view and focus to provide feedback on measurement suitability, in accordance with various embodiments.

FIG. 4 is a flow chart 400 illustrating exemplary steps 402-416 that may be utilized for automatically detecting an ultrasound image view 310 and focus to provide feedback 320-336 on measurement suitability, in accordance with various embodiments. Referring to FIG. 4, there is shown a flow chart 400 comprising exemplary steps 402 through 416. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, an ultrasound system 100 acquires ultrasound image 310 of a target. For example, the ultrasound system 100 may acquire ultrasound image views 310, such as a four chamber (4CH) or parasternal long-axis (PLAX) view, with an ultrasound probe 104 positioned at a scan position over a heart.

At step 404, a signal processor 132 of the ultrasound system 100 automatically identifies an ultrasound image view 310 and focus based on detected anatomical structures in the ultrasound image 310. For example, an image view detection processor 140 of the signal processor 132 may be configured to apply image analysis algorithms, artificial intelligence algorithms, one or more deep neural networks (e.g., a convolutional neural network) and/or any suitable form of image analysis techniques or machine learning processing functionality to ultrasound images 310 acquired at step 402 to automatically identify an ultrasound image view 310 and focus.

At step 406, the signal processor 132 of the ultrasound system 100 may automatically select one or more measurements 320 associated with the detected anatomical structures 330 in the identified ultrasound image view 310. For example, a measurement identification processor 150 of the signal processor 132 may be configured to automatically select one or more measurements 320 associated with anatomical structures 330 in the ultrasound image view 310 identified by the image view detection processor 140 at step 404. For example, ultrasound image views may each be associated with one or more potentially relevant measurements 320. The one or more potentially relevant measurements 320 associated with one or more ultrasound image views 310 may be stored at archive 138 and/or any suitable data storage medium. The measurement identification processor 150 may be configured to select the one or more potentially relevant measurements 320 from the archive 138 and/or any suitable data storage medium based on the association and the ultrasound image view 310 identified by the image view detection processor 140. The measurement identification processor 150 may be configured to present the selected one or more potentially relevant measurements 320 at the display system 134.

At step 408, the signal processor 132 of the ultrasound system 100 may automatically analyze the ultrasound image 310 and assign a grade 322, 324, 326 for each of the selected measurements 320 based on an ability to accurately perform each measurement 320 in the ultrasound image 310. For example, a measurement grading processor 160 of the signal processor 132 may apply image analysis algorithms, artificial intelligence algorithms, one or more deep neural networks (e.g., a convolutional neural network) and/or any suitable form of image analysis techniques or machine learning processing functionality to the ultrasound images acquired 310 at step 402 and assign grades 322, 324, 326 to the measurements 320 selected at step 406. The measurement grading processor 160 may further assign grades 332, 334, 336 to anatomical structures 330 associated with the measurements 320 selected at step 406. The measurement grading processor 160 may assign the grades 322, 324, 326, 332, 334, 336 based on a level of completeness of the anatomical structure to be measured, a focus level of the anatomical structure to be measured, and/or any suitable criterion related to the image quality of the anatomical structure to be measured.

At step 410, the signal processor 132 of the ultrasound system 100 may present the grade 322, 324, 326 for each of the selected measurements 320 at a display system 134. For example, the measurement grading processor 160 of the signal processor 132 may be configured to cause the display system 134 to present the grade 322, 324, 326, 332, 334, 336 derived from the image quality criterion for each of the selected measurements 320 and/or anatomical structures 330. The grades 322, 324, 326, 332, 334, 336 may include a plurality of grade levels, such as ideal for measurement, suitable for measurement, and not suitable for measurement, or any suitable number of grade levels. The grade levels may be represented by symbols (e.g., check mark for suitable and "X" for not suitable), color-coding (e.g., green for ideal, orange for suitable, and red for not suitable), numerical grade levels, letter grade levels, text describing suitability, and/or any suitable grade level indicator. In various embodiments, the grade levels may correspond with whether the measurement may be performed automatically by the signal processor 132, whether the measurement may be performed manually by a user via the user input device 130, and/or whether the measurement may not be performed.

At step 412, the process 400 may return to stop 402 if the ultrasound probe 104 is moved. Additionally and/or alternatively, the process 400 may proceed to step 414 if the ultrasound probe 104 is not moved. For example, an ultrasound operator may reposition the ultrasound probe 104 of the ultrasound system 100 if the operator is not satisfied with the detected ultrasound image view, the feedback 320-336 on measurement suitability, such as the grades 322, 326, 328, 332, 334, 336 related to the selected measurements 320 and/or anatomical structures 330, or the feedback related to the ability to perform automated and/or manual measurements 328. The ultrasound operator may maintain the position of the ultrasound probe 104 based on favorable measurement suitability feedback 320-336.

At step 414, the signal processor 132 of the ultrasound system 100 may receive a selection 328 to automatically or manually perform one or more of the selected measurements 320. For example, the measurement grading processor 160 may provide a selectable option 328 to perform a corresponding measurement 320. For example, the selectable option 328 may indicate whether the measurement 320 may be performed automatically or manually. In various embodiments, an ability to automatically perform the measurement 320 by the signal processor 132 may be based on the measurement suitability grade 322, 324, 326. The selectable measurement option 328 may be buttons, a drop down menu, and/or any suitable selectable option. The signal processor 132 may receive a selection to automatically or manually perform one or more of the selected measurements 320 via user input device 130.

At step 416, the signal processor 132 of the ultrasound system 100 may perform and present the one or more selected measurements 320 at the display system 134. For example, a selection of the automatic measurement option 328 of a particular measurement 320 at step 414 may initiate an automatic measurement performed by the signal processor 132 and presented at the display system 134. As another example, selection of the manual measurement option 328 of a particular measurement 320 at step 414 may initiate a manual measurement mode where measurement tools are presented such that an operator may manually perform the selected measurement 320 for presentation at the display system 134.

Aspects of the present disclosure provide a method 400 and system 100 for automatically detecting an ultrasound image view 310 and focus to provide feedback 320-336 on measurement suitability. In accordance with various embodiments, the method 400 may comprise acquiring 402, by an ultrasound system 100, an ultrasound image 310 of a target. The method 400 may comprise automatically identifying 404, by at least one processor 132, 140 of the ultrasound system 100, an ultrasound image view 310 and focus based on detected anatomical structures in the ultrasound image 310. The method 400 may comprise automatically selecting 406, by the at least one processor 132, 150, at least one measurement 320 associated with the ultrasound image view 310. The method 400 may comprise assigning 408, by the at least one processor 132, 150, a measurement grade 322, 324, 326 for each of the at least one measurements 320 based on an ability to accurately perform each of the at least one measurement 320 in the ultrasound image 310. The method 400 may comprise causing 410, by the at least one processor 132, 140, 150, 160, a display system 134 to present the measurement grade 322, 324, 326 for each of the at least one measurement 320.

In an exemplary embodiment, the method 400 may comprise receiving 414, by the at least one processor 132, a selection 328 to perform one of the at least one measurement 320. In a representative embodiment, the method 400 may comprise automatically performing 416, by the at least one processor 132, the one of the at least one measurement 320 in response to receiving the selection 328. The method 400 may comprise causing 416, by the at least one processor 132, the display system 134 to present results of the one of the at least one measurement 320. In various embodiments, the method 400 may comprise causing 416, by the at least one processor 132, the display system 134 to present measurement tools for manually performing the one of the at least one measurement 320 in response to receiving the selection 328. In certain embodiments, the ability to accurately perform each of the at least one measurement 320 in the ultrasound image 310 may be based on a completeness of the detected anatomical structures in the ultrasound image 310 and a focus level of the detected anatomical structures in the ultrasound image 310. In an exemplary embodiment, the measurement grade 322, 324, 326 may be one of a plurality of grade levels, each of the plurality of grade levels represented by one or more of a symbol, color-coding, a numerical grade level, a letter grade level, or a text description of the grade level. In a representative embodiment, the method 400 may comprise assigning 408, by the at least one processor 132, 160, an anatomical structure grade 332, 334, 336 for each of the detected anatomical structures 330 in the ultrasound image 310. The method 400 may comprise causing 410, by the at least one processor 132, 140, 150, 160, a display system 134 to present the anatomical structure grade 332, 334, 336 for each of the detected anatomical structures 330.

Various embodiments provide a system 100 for automatically detecting an ultrasound image view 310 and focus to provide feedback 320-336 on measurement suitability. The system 100 may comprise an ultrasound system 100, at least one processor 132, 140, 150, 160, and a display system 134. The ultrasound system 100 may be configured to acquire an ultrasound image 310 of a target. The at least one processor 132, 140 may be configured to automatically identify an ultrasound image view 310 and focus based on detected anatomical structures in the ultrasound image 310. The at least one processor 132, 150 may be configured to automatically select at least one measurement 320 associated with the ultrasound image view 310. The at least one processor 132, 160 may be configured to assign a measurement grade 322, 324, 326 for each of the at least one measurements 320 based on an ability to accurately perform each of the at least one measurement 320 in the ultrasound image 310. The display system 134 may be configured to present the measurement grade 322, 324, 326 for each of the at least one measurement 320.

In a representative embodiment, the at least one processor 132 may be configured to receive a selection 328 to perform one of the at least one measurement 320. In various embodiments, the at least one processor 132 may be configured to automatically perform the one of the at least one measurement 320 in response to receiving the selection 328. The display system 134 may be configured to present results of the one of the at least one measurement 320. In certain embodiments, the display system 134 may be configured to present measurement tools for manually performing the one of the at least one measurement 320 in response to the at least one processor 132 receiving the selection 328. In an exemplary embodiment, the ability to accurately perform each of the at least one measurement 320 in the ultrasound image 310 may be based on a completeness of the detected anatomical structures in the ultrasound image 310 and a focus level of the detected anatomical structures in the ultrasound image 310. In a representative embodiment, the measurement grade 322, 324, 326 may be one of a plurality of grade levels. Each of the plurality of grade levels represented by one or more of a symbol, color-coding, a numerical grade level, a letter grade level, or a text description of the grade level. In various embodiments, the at least one processor 132, 160 may be configured to assign an anatomical structure grade 332, 334, 336 for each of the detected anatomical structures 330 in the ultrasound image 310. The display system 134 may be configured to present the anatomical structure grade 332, 334, 336 for each of the detected anatomical structures 330.

Certain embodiments provide a non-transitory computer readable medium having stored thereon, a computer program having at least one code section. The at least one code section is executable by a machine for causing the machine to perform steps 400. The steps 400 may comprise receiving 402 an ultrasound image 310 of a target. The steps 400 may comprise automatically identifying 404 an ultrasound image view 310 and focus based on detected anatomical structures in the ultrasound image 310. The steps 400 may comprise automatically selecting 406 at least one measurement 320 associated with the ultrasound image view 310. The steps 400 may comprise assigning 408 a measurement grade 322, 324, 326 for each of the at least one measurements 320 based on an ability to accurately perform each of the at least one measurement 320 in the ultrasound image 310. The steps 400 may comprise causing 410 a display system 134 to present the measurement grade 322, 324, 326 for each of the at least one measurement 320.

In various embodiments, the steps 400 may comprise receiving 414 a selection 328 to perform one of the at least one measurement 320. The steps 400 may comprise automatically performing 416 the one of the at least one measurement 320 in response to receiving the selection 328. The steps 400 may comprise causing 416 the display system 134 to present results of the one of the at least one measurement 320. In certain embodiments, the steps 400 may comprise receiving 414 a selection 328 to perform one of the at least one measurement 320. The steps 400 may comprise causing 416 the display system 134 to present measurement tools for manually performing the one of the at least one measurement 320 in response to receiving the selection 328. In an exemplary embodiment, the ability to accurately perform each of the at least one measurement 320 in the ultrasound image 310 may be based on a completeness of the detected anatomical structures in the ultrasound image 310 and a focus level of the detected anatomical structures in the ultrasound image 310. In a representative embodiment, the measurement grade 322, 324, 326 may be one of a plurality of grade levels, each of the plurality of grade levels represented by one or more of a symbol, color-coding, a numerical grade level, a letter grade level, or a text description of the grade level. In various embodiments, the steps 400 may comprise assigning 408 an anatomical structure grade 332, 334, 336 for each of the detected anatomical structures 330 in the ultrasound image 310. The steps 400 may comprise causing 410 a display system 134 to present the anatomical structure grade 332, 334, 336 for each of the detected anatomical structures 330.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically detecting an ultrasound image view and focus to provide feedback on measurement suitability.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
    acquiring, by an ultrasound system, an ultrasound image of a target;
    automatically identifying, by at least one processor of the ultrasound system, an ultrasound image view from a plurality of ultrasound image views based on detected anatomical structures present in the ultrasound image, wherein each of the plurality of ultrasound image views is associated with at least one specific measurement;
    automatically selecting, by the at least one processor, the at least one specific measurement based on the identified ultrasound image view, wherein each of the at least one specific measurement is a measurement of one or more of the detected anatomical structures in the ultrasound image;
    assigning, by the at least one processor, a measurement grade for each of the at least one specific measurement, wherein each of the measurement grade represents an ability to accurately perform a corresponding one of the at least one specific measurement in the ultrasound image; and
    causing, by the at least one processor, a display system to simultaneously present an identification of each of the at least one specific measurement and the measurement grade for each of the at least one specific measurement, prior to performance of any of the at least one specific measurement.

2. The method of claim 1, comprising receiving, by the at least one processor, a selection input by a user of the ultrasound system to perform one of the at least one specific measurement.

3. The method of claim 2, comprising:
    automatically performing, by the at least one processor, the one of the at least one specific measurement in response to receiving the selection, and
    causing, by the at least one processor, the display system to present results of the one of the at least one specific measurement.

4. The method of claim 2, comprising causing, by the at least one processor, the display system to present measurement tools for manually performing the one of the at least one specific measurement in response to receiving the selection.

5. The method of claim 1, wherein the ability to accurately perform the corresponding one of the at least one specific measurement in the ultrasound image is based on a completeness of the detected anatomical structures in the ultrasound image and a focus level of the detected anatomical structures in the ultrasound image.

6. The method of claim 1, wherein the measurement grade is one of a plurality of grade levels, each of the plurality of grade levels represented by one or more of:
    a symbol,
    color-coding,
    a numerical grade level,
    a letter grade level, or
    a text description of the grade level.

7. The method of claim 1, comprising:
    assigning, by the at least one processor, an anatomical structure grade for each of the detected anatomical structures in the ultrasound image, and
    causing, by the at least one processor, a display system to present the anatomical structure grade for each of the detected anatomical structures.

8. A system comprising:
    an ultrasound system configured to acquire an ultrasound image of a target;
    at least one processor configured to:
        automatically identify an ultrasound image view from a plurality of ultrasound image views based on detected anatomical structures present in the ultrasound image, wherein each of the plurality of ultrasound image views is associated with at least one specific measurement;
        automatically select the at least one specific measurement based on the identified ultrasound image view, wherein each of the at least one specific measurement is a measurement of one or more of the detected anatomical structures in the ultrasound image; and
        assign a measurement grade for each of the at least one specific measurement, wherein each of the measurement grade represents an ability to accurately perform a corresponding one of the at least one specific measurement in the ultrasound image; and
    a display system configured to simultaneously present an identification of each of the at least one specific measurement and the measurement grade for each of the at least one specific measurement, prior to performance of any of the at least one specific measurement.

9. The system of claim 8, wherein the at least one processor is configured to receive a selection input by a user of the ultrasound system to perform one of the at least one specific measurement.

10. The system of claim 9, wherein:
    the at least one processor is configured to automatically perform the one of the at least one specific measurement in response to receiving the selection, and
    the display system is configured to present results of the one of the at least one specific measurement.

11. The system of claim 9, wherein the display system is configured to present measurement tools for manually performing the one of the at least one specific measurement-in response to the at least one processor receiving the selection.

12. The system of claim 8, wherein the ability to accurately perform the corresponding one of the at least one specific measurement in the ultrasound image is based on a completeness of the detected anatomical structures in the ultrasound image and a focus level of the detected anatomical structures in the ultrasound image.

13. The system of claim 8, wherein the measurement grade is one of a plurality of grade levels, each of the plurality of grade levels represented by one or more of:
    a symbol,
    color-coding,
    a numerical grade level,
    a letter grade level, or
    a text description of the grade level.

14. The system of claim 8, wherein:
- the at least one processor is configured to assign an anatomical structure grade for each of the detected anatomical structures in the ultrasound image, and
- the display system is configured to present the anatomical structure grade for each of the detected anatomical structures.

15. A non-transitory computer readable medium having stored thereon, a computer program having at least one code section, the at least one code section being executable by a machine for causing the machine to perform steps comprising:
- receiving an ultrasound image of a target;
- automatically identifying an ultrasound image view from a plurality of ultrasound image views based on detected anatomical structures present in the ultrasound image, wherein each of the plurality of ultrasound image views is associated with at least one specific measurement;
- automatically selecting the at least one specific measurement based on the identified ultrasound image view, wherein each of the at least one specific measurement is a measurement of one or more of the detected anatomical structures in the ultrasound image;
- assigning a measurement grade for each of the at least one specific measurement, wherein each of the measurement grade represents an ability to accurately perform a corresponding one of the at least one specific measurement in the ultrasound image; and
- causing a display system to simultaneously present an identification of each of the at least one specific measurement and the measurement grade for each of the at least one specific measurement, prior to performance of any of the at least one specific measurement.

16. The non-transitory computer readable medium of claim 15, comprising:
- receiving a selection input by a user of an ultrasound system to perform one of the at least one specific measurement,
- automatically performing the one of the at least one specific measurement in response to receiving the selection, and
- causing the display system to present results of the one of the at least one specific measurement.

17. The non-transitory computer readable medium of claim 15, comprising:
- receiving a selection input by a user of an ultrasound system to perform one of the at least one specific measurement, and
- causing the display system to present measurement tools for manually performing the one of the at least one specific measurement in response to receiving the selection.

18. The non-transitory computer readable medium of claim 15, wherein the ability to accurately perform the corresponding one of the at least one specific measurement in the ultrasound image is based on a completeness of the detected anatomical structures in the ultrasound image and a focus level of the detected anatomical structures in the ultrasound image.

19. The non-transitory computer readable medium of claim 15, wherein the measurement grade is one of a plurality of grade levels, each of the plurality of grade levels represented by one or more of:
- a symbol,
- color-coding,
- a numerical grade level,
- a letter grade level, or
- a text description of the grade level.

20. The non-transitory computer readable medium of claim 15, comprising:
- assigning an anatomical structure grade for each of the detected anatomical structures in the ultrasound image, and
- causing a display system to present the anatomical structure grade for each of the detected anatomical structures.

* * * * *